United States Patent [19]  
von Bittera et al.

[11] Patent Number: 4,457,938  
[45] Date of Patent: Jul. 3, 1984

[54] ANTIMYCOTIC AGENT, IN THE FORM OF STICKS, WITH A HIGH RELEASE OF ACTIVE COMPOUND

[75] Inventors: Miklos von Bittera, Leverkusen; Karl H. Büchel, Burscheid; Manfred Plempel; Erik Regel, both of Wuppertal, all of Fed. Rep. of Germany

[73] Assignee: Bayer Aktiengesellschaft, Leverkusen, Fed. Rep. of Germany

[21] Appl. No.: 346,479

[22] Filed: Feb. 5, 1982

[30] Foreign Application Priority Data

Feb. 23, 1981 [DE] Fed. Rep. of Germany ....... 3106635

[51] Int. Cl.$^3$ ............................................. A61K 31/415
[52] U.S. Cl. ........................... 424/273 R; 424/DIG. 5
[58] Field of Search ...................... 424/DIG. 5, 273 R

[56] References Cited

U.S. PATENT DOCUMENTS

| | | | |
|---|---|---|---|
| 2,799,613 | 7/1957 | Blodorn | 424/64 |
| 3,856,931 | 12/1974 | Fuchs et al. | 424/14 |
| 3,899,578 | 8/1975 | Bird et al. | 424/81 |
| 3,903,287 | 9/1975 | Meiser et al. | 424/273 |
| 4,118,487 | 10/1978 | Regel et al. | 424/273 R |
| 4,268,498 | 5/1981 | Gedeon et al. | 424/DIG. 5 |
| 4,301,166 | 11/1981 | Regel et al. | 424/273 R |

OTHER PUBLICATIONS

Chem. Abs. 73:23458b (1970), "Fungus Damage and its Prevention in Tissues Preserved in a Polymer", Chaika et al.
Merck Index, 9th Edition, "Clotrimazole" 2370, p. 309 (1976).

Primary Examiner—Jerome D. Goldberg  
Assistant Examiner—Freda L. Abramson  
Attorney, Agent, or Firm—Sprung, Horn, Kramer & Woods

[57] ABSTRACT

The invention relates to stick formulations of antimycotic azole derivatives containing, in addition to the antimycotic azole derivatives, 3 to 5% by weight relative to the formulation, of benzyl alcohol, 2.5 to 10% by weight, relative to the formulation of spreading agent and one or more auxiliaries.

6 Claims, No Drawings

ANTIMYCOTIC AGENT, IN THE FORM OF STICKS, WITH A HIGH RELEASE OF ACTIVE COMPOUND

The present invention relates to certain novel and unobvious formulations of certain known antimycotic azole derivatives, which exhibit a higher release of active compounds and accordingly make short-duration therapy possible.

Formulations of antimycotic derivatives for the treatment of mycoses in warm-blooded animals, especially mycoses of the skin and of the skin appendages, have already been disclosed. With these formulations, the duration of therapy required for complete cure was 14 to 21 days.

In order to achieve a shortening of the duration of therapy a higher release of the active compounds in an aqueous medium is required, especially in order to eliminate the germs, and in order thereby to achieve a mycologically reliable cure. The known formulations are only of limited suitability for this purpose, because only a small proportion of the active compound made available dissolves in the volume of liquid—that is to say dissolves at the locus of the infection. If it is now desired to achieve a shortening of the duration of therapy, for example to one day with a single application, without further increasing the concentration of active compound, it is necessary to ensure optimum release of the active compound.

According to the present invention there is provided a stick formulation of an antimycotic agent, with higher release of the antimycotic active compound(s), containing one or more antimycotic azole derivatives, 3 to 5% by weight, relative to the formulation, of benzyl alcohol, 2.5 to 10% by weight, relative to the formulation, a spreading agent, and one or more stick formulation auxiliaries.

The stick formulations of the present invention release the active compound to a greater degree than the mentioned prior formulations and as a result permit shortening the duration of therapy to 1 day. This effect of higher release of active compound can be as much as a power of ten.

Active compounds which can be formulated in this manner are any of the antimycotically active derivatives, especially antimycotically active imidazole derivatives and triazole derivatives. They are present in the agents according to the invention in amounts of 0.05 to 1% by weight, preferably of 0.1 to 1% by weight, relative to the weight of the formulation.

By way of example, the compounds of the following formulae may be mentioned as preferred antimycotic agents:

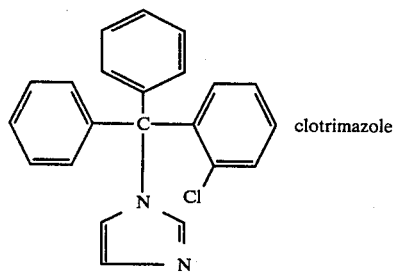

clotrimazole (I)

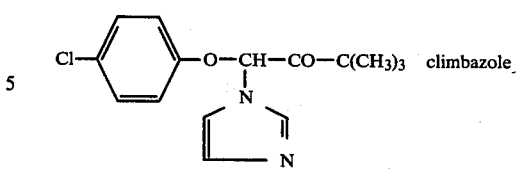

climbazole (II)

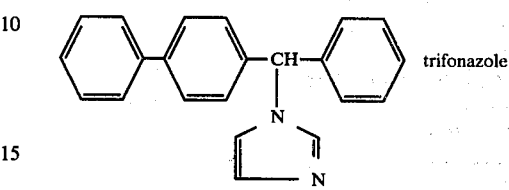

trifonazole (III)

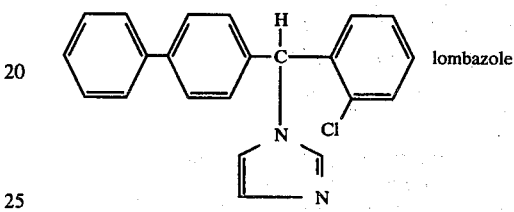

lombazole (IV)

Numerous other antimycotically active azole derivatives are known from DE-OS (German Published Specification) No. 2,430,039. They can also serve as active compounds in the agents according to the invention.

By spreading agents, there are understood oily liquids which spread particularly well on the skin, [R. Keymer, Pharm. Ind. 32 1970, 577–581]. Particularly suitable spreading agents for use in the in the formulations according to the invention are the following compounds:

Silicone oils of various viscosities.

Fatty acid esters, such as ethyl stearate, di-n-butyl adipate, hexyl laurate, dipropylene glycol pelargonate, esters of a branched fatty acid of medium chain length with saturated $C_{16}$–$C_{18}$ fatty alcohols, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck preen gland fat, dibutyl phthalate, diisopropyl adipate, ester mixtures related to the latter, myristyl lactate, cetyl lactate, 2-ethylhexyl palmitate and myristyl myristate.

Triglycerides, such as caprylic/capric acid triglyceride, triglyceride mixtures with vegetable fatty acids of chain length $C_8$–$C_{12}$ or other specially selected natural fatty acids, partial glyceride mixtures of saturated or unsaturated fatty acids, which optionally also contain hydroxyl groups and monoglycerides of $C_8$/$C_{10}$-fatty acids.

Fatty alcohols, such as isotridecyl alcohol, 2-octyldodecanol, cetyl/stearyl alcohol and oleyl alcohol.

Fatty acids, such as, for example, oleic acid.

Particularly suitable spreading oils are the following: isopropyl myristate, isopropyl palmitate, caprylic/capric acid esters of saturated fatty alcohols of chain length $C_{12}$–$C_{18}$, waxy fatty acid esters such as synthetic duck preen gland fat, silicone oils, and an isopropyl myristate/isopropyl stearate/isopropyl palmitate mixture.

The following further auxiliaries and/or basic formulation auxiliaries can be used in the preparation of the agents according to the invention:

non-ionic emulsifiers prepared by reacting higher saturated fatty alcohols with ethylene oxide. Sodium stearate, cetyl/stearyl alcohol, stearic acid, 2-octyldodecanol (Guerbet alcohol), "glyceryl stearates", a mixture of fatty alcohols, waxes and oils, a mixture of monoglycerides and diglycerides of palmitic acid and stearic acid, coconut fatty acid monoethanolamide, a colloidal disperse mixture of cetyl/stearyl alcohol, and sodium cetyl/stearyl-sulphate, decyl oleate, n-hexadecanol, lauric acid monoethanolamide, cetyl palmitate and slightly crosslinked polyacrylic acid of extremely high molecular weight. Glycerol, high viscosity paraffin, low viscosity paraffin, triethanolamine, collagen, allantoin, novantisolic acid, perfume oils, sodium hydroxide, propylene glycol, dipropylene glycol and tripropylene glycol and waxes.

Further suitable materials are:

a. Substances, which, for example, can stabilise a suspension, for example colloidal silica and montmorillonite.

b. Surfactants (this includes emulsifiers and wetting agents), for example 1. anionic surfactants, such as Na laurylsulphate, fatty alcohol-ether-sulphates, monoalkyl-/dialkyl-polyglycol-ether orthophosphoric acid ester monoethanolamine salt;

2. cationic surfactants, such as cetyltrimethylammonium chloride;

3. ampholytic surfactants, such as di-Na-N-lauryl-$\beta$-iminodipropionate or lecithin;

4. non-ionic surfactants, for example polyoxyethylated castor oil, polyoxyethylated sorbitan monooleate, sorbitan monostearate, cetyl alcohol and glycerol monostearate, polyoxyethylene stearate and alkylphenol polyglycol ethers.

c. Stabilisers for preventing the chemical degradation which occurs with some active compounds, such as antioxidants, for example tocopherols and butylhydroxyanisole.

Suitable gel-forming agents are macromolecular compounds which can dissolve or swell both in water and in organic solvents and which, after drying, form a type of film.

If a classification of the macromolecular auxiliaries [Keipert et al., Die Pharmazie 28 1973, 145–183] is followed, it is above all ionic macromolecules, in their salt form, which are employed. They include, inter alia, sodium carboxymethylcellulose, polyacrylic acid, polymethacrylic acid and their salts, sodium amylopectin-semiglycolate, alginic acid and propylene glycol alginate as the sodium salt, gum arabic, xanthan gum and guar gum.

Amphoteric macromolecules, such as protein derivatives, for example gelatins, are just as suitable as non-ionic polymers, for example methylcellulose, hydroxypropylcellulose and soluble starches, which conform to the above requirements.

Suitable solvents are water as well as any of the water-miscible solvents. It is possible to use, for example, alkanols, such as ethanol and isopropyl alcohol, propylene glycol, methyl CELLOSOLVE (ethylene glycol monomethyl ether), CELLOSOLVE (ethylene glocyl monoethyl ether) esters, morpholines, dioxane, dimethylsulphoxide, dimethylformamide, tetrahydrofuran and cyclohexanone.

One or more solvents can be employed in the preparation of the formulations according to the invention.

The following Examples 1 to 6 illustrate stick formulations according to the present invention.

In each of these Examples and also Comparative Examples A and B the sticks were prepared as follows:

The individual components were fused or dissolved at 70° C. to 75° C. The finished mix was deaerated by leaving the mass, in the dissolved state, to stand for quarter of an hour. Heating the melt for too long, and to a higher temperature than necessary, was to be avoided. The sticks were cast at about 70° C. No air was allowed to be trapped thereby. A glossy surface was achieved by passing a flame over the sticks.

Comparative Example A

Stick contained neither benzyl alcohol nor spreading agent

| | |
|---|---|
| Trifonazole (active compound) | 1.00 |
| Non-ionic emulsifier prepared by reacting higher saturated fatty alcohols with ethylene oxide | 5.00 |
| sodium stearate | 8.00 |
| 1,2-Propylene glycol | 15.00 |
| Anhydrous glycerol | 15.00 |
| Demineralised water | 13.00 |
| Ethanol to make up to | 100.00 |

Comparative Example B

Stick contained benzoyl alcohol but no spreading agent

| | |
|---|---|
| Trifonazole (active compound) | 1.00 |
| Non-ionic emulsifier prepared by reacting higher saturated fatty alcohols with ethylene oxide | 5.00 |
| Sodium stearate | 8.00 |
| 1,2-Propylene glycol | 15.00 |
| Anhydrous glycerol | 15.00 |
| Demineralised water | 10.00 |
| Benzyl alcohol | 3.00 |
| Ethanol to make up to | 100.00 |

Example 1

| | |
|---|---|
| Trifonazole (active compound) | 1.00 |
| Non-ionic emulsifier prepared by reacting higher saturated fatty alcohols with ethylene oxide | 5.00 |
| Sodium stearate | 8.00 |
| 1,2-Propylene glycol | 10.00 |
| Anhydrous glycerol | 10.00 |
| Water | 10.00 |
| Isopropyl myristate | 10.00 |
| Benzyl alcohol | 3.00 |
| Perfume oil | 1.00 |
| Ethanol to make up to | 100.00 |

Example 2

| | |
|---|---|
| Clotrimazole (active compound) | 1.00 |
| Cetyl/stearyl alcohol | 5.00 |
| Sodium stearate | 8.00 |
| 1,2-Propylene glycol | 10.00 |
| Anhydrous glycerol | 10.00 |
| Water | 10.00 |
| Isopropyl myristate | 10.00 |
| Benzyl alcohol | 3.00 |
| Perfume oil | 1.00 |
| Ethanol to make up to | 100.00 |

Example 3

| | |
|---|---|
| Lombazole (active compound) | 1.00 |
| Non-ionic emulsifier prepared by reacting higher saturated fatty alcohols with ethylene oxide | 5.00 |
| Sodium stearate | 8.00 |
| 1,2-Propylene glycol | 10.00 |
| Anhydrous glycerol | 10.00 |
| Demineralised water | 10.00 |
| Isopropyl myristate | 10.00 |
| Benzyl alcohol | 3.00 |
| Perfume oil | 1.00 |
| Ethanol to make up to | 100.00 |

Example 4

| | |
|---|---|
| Lombazole (active compound) | 0.10 |
| Non-ionic emulsifier prepared by reacting higher saturated fatty alcohols with ethylene oxide | 5.00 |
| Sodium stearate | 8.00 |
| 1,2-Propylene glycol | 10.00 |
| Anhydrous glycerol | 10.00 |
| Demineralised water | 10.00 |
| Isopropyl myristate | 10.00 |
| Benzyl alcohol | 3.00 |
| Perfume oil | 1.00 |
| Ethanol to make up to | 100.00 |

Example 5

| | |
|---|---|
| Trifonazole (active compound) | 1.00 |
| Sodium stearate | 6.00 |
| Demineralised water | 5.00 |
| 1,2-Propylene glycol | 22.50 |
| Isopropyl myristate | 2.50 |
| Benzyl alcohol | 3.00 |
| Perfume oil | 1.00 |
| Ethanol to make up to | 100.00 |

Example 6

| | |
|---|---|
| Climbazole (active compound) | 1.00 |
| Non-ionic emulsifier prepared by reacting higher saturated fatty alcohols with ethylene oxide | 5.00 |
| Sodium stearate | 8.00 |
| 1,2-Propylene glycol | 10.00 |
| Anhydrous glycerol | 10.00 |
| Water | 10.00 |
| Isopropyl myristate | 10.00 |
| Benzyl alcohol | 3.00 |
| Prefume oil | 1.00 |
| Ethanol to make up to | 100.00 |

Test of the activity of the agent according to the invention on Trichophyton-infected guineapigs As the test model for the comparative activity test of the formulations according to the invention, Trichophyton-infected Pirbright white guineapigs having an average weight of 600 g were used. The backs of the animals were shorn with an electric hair-cutter, so that about 1/10 mm long hair stumps were left.

The infection with Trichophyton mentagrophytes was effected by lightly rubbing a spore suspension of the causative organism, germinated in Sabouraud nutrient solution for 24 hours, over an area of size about 2×2 cm of the shorn backs of the animals. Per animal, 0.5 ml of germ suspension, containing $1-3 \times 10^5$ infectious fungal particles, was applied.

With this mode of infection, the first symptoms of the dermatophytosis manifested themselves 2–3 days after infection as redness and scurfing of the skin. In untreated animals, the dermatophytosis was most pronounced about 14 days after infection: loss of hair over entire areas, and bleeding integument defects within an inflammatorily modified, scurfy edge zone.

The formulations to be tested were applied *once,* on the second day after infection, locally onto the reddened infection area of the animals, and lightly rubbed in with a horn spatula. In each case, 0.5 ml of the formulation = 5 mg of active compound (1% strength formulation) was applied. The course of the infection was assessed daily up to the 20th day after infection.

The test results can be seen from the table which follows:

| Agent from Example | Action on Trichophyton-infected guinea pigs |
|---|---|
| A | ** |
| B | *** |
| 1 | **** |
| 2 | **** |
| 3 | **** |
| 4 | **** |
| 5 | **** |
| 6 | **** |

****: very good action
***: good action
**: action
*: weak action
0: no action

If in place of the formulations according to the invention, formulations which contain no benzyl alcohol and no spreading agent (as in Comparative Examples A and B) were used, as effect corresponding to that of the formulations according to the invention could only be achieved after three applications.

We claim:

1. A stick formulation of an antimycotic agent, with higher release of the antimycotic active compound(s), containing 0.05 to 1% by weight of an antimycotic azole derivatives selected from the group consisting of clotrimazole, trifonazole, climbazole, lombazole and mixtures of said compounds, 3 to 5% by weight, relative to the formulation, of benzyl alcohol, 2.5 to 10% by weight, relative to the formulation of isopropyl myristate and one or more stick formulation auxiliaries.

2. A stick formulation according to claim 1, in which the antimycotic azole derivative is clotrimazole of the formula

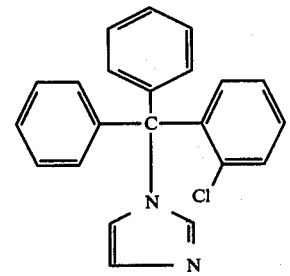

3. A stick formulation according to claim 1 in which the antimycotic azole derivative is trifonazole of the formula

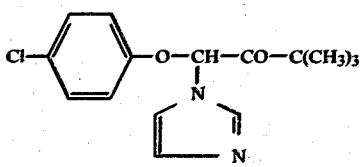

5. A stick formulation according to claim 1, in which the antimycotic azole derivative is lombazole of the formula

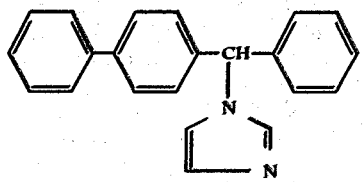

4. A stick formulation according to claim 1, in which the antimycotic azole derivative is climbazole of the formula

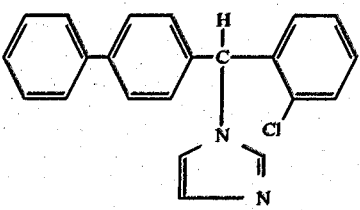

6. A stick formulation according to any of claims 1 to 5, in which the antimycotic azole derivative is present in an amount of 0.1 to 1% by weight, relative to the weight of the formulation.

* * * * *